(12) United States Patent
Bassez et al.

(10) Patent No.: US 11,364,149 B2
(45) Date of Patent: Jun. 21, 2022

(54) ELASTIC VENOUS COMPRESSION ORTHOSIS

(71) Applicant: LABORATOIRES INNOTHERA, Arcueil (FR)

(72) Inventors: Sophie Bassez, Villebon sur Yvette (FR); Amina Ouchene, Cretell (FR); Jean-Christophe Lourme, Villebon sur Yvette (FR); Grégory Vaucoux, L'Hay les Roses (FR)

(73) Assignee: LABORATOIRES INNOTHERA, Arcueil (FR)

( * ) Notice: Subject to any disclaimer, the term of this patent is extended or adjusted under 35 U.S.C. 154(b) by 0 days.

(21) Appl. No.: 15/598,953

(22) Filed: May 18, 2017

(65) Prior Publication Data

US 2017/0333256 A1 Nov. 23, 2017

(30) Foreign Application Priority Data

May 18, 2016 (FR) ...................... 16 54389

(51) Int. Cl.
*A61F 13/00* (2006.01)
*A61F 13/08* (2006.01)
*G07C 3/04* (2006.01)
*A61B 5/053* (2021.01)
*A61B 5/00* (2006.01)
*A61F 5/01* (2006.01)

(52) U.S. Cl.
CPC ........ *A61F 13/00051* (2013.01); *A61B 5/053* (2013.01); *A61B 5/4833* (2013.01); *A61B 5/6807* (2013.01); *A61F 5/0102* (2013.01); *A61F 13/08* (2013.01); *G07C 3/04* (2013.01); *A61F 2005/0188* (2013.01)

(58) Field of Classification Search
CPC .. A61F 13/00051; A61F 13/08; A61B 5/4833; A61B 5/1121; A61C 19/04
See application file for complete search history.

(56) References Cited

U.S. PATENT DOCUMENTS

| | | | | |
|---|---|---|---|---|
| 4,454,871 A * | 6/1984 | Mann | .................... | A61F 5/0111 602/27 |
| 5,185,000 A * | 2/1993 | Brandt | .................. | A61F 5/0111 2/22 |
| 7,192,411 B2 * | 3/2007 | Gobet | ..................... | A61F 13/08 2/239 |
| 7,632,216 B2 * | 12/2009 | Rahman | ............... | A61B 5/4833 482/1 |
| 9,237,869 B1 * | 1/2016 | Lee | ....................... | A61B 5/6802 |

(Continued)

FOREIGN PATENT DOCUMENTS

| | | |
|---|---|---|
| GB | 2027902 A | 2/1980 |
| WO | 2012/107571 A1 | 8/2012 |

(Continued)

OTHER PUBLICATIONS

"Orthotimer" (Jan. 18, 2016)URL:http://web.archive.org/web/20160118223724/http://www.orthotimer.com/index-en.html.

(Continued)

*Primary Examiner* — Matthew Kremer
(74) *Attorney, Agent, or Firm* — Oliff PLC

(57) ABSTRACT

An orthosis, in particular an elastic venous compression orthosis, provided with a device for measuring the time during which the orthosis is worn.

14 Claims, 1 Drawing Sheet

(56) References Cited

U.S. PATENT DOCUMENTS

| | | | |
|---|---|---|---|
| 9,642,529 B1* | 5/2017 | Siddiqui | G16H 50/20 |
| 9,734,295 B1* | 8/2017 | Movva | A61B 5/1127 |
| 9,781,842 B2* | 10/2017 | Tai | H05K 3/284 |
| 2011/0092867 A1* | 4/2011 | Watts | A61F 5/0111 |
| | | | 602/27 |
| 2013/0218061 A1* | 8/2013 | Cowan | A61F 5/0111 |
| | | | 602/28 |
| 2015/0125839 A1* | 5/2015 | Tillges | A61F 5/0102 |
| | | | 434/262 |
| 2015/0135310 A1* | 5/2015 | Lee | H04W 12/065 |
| | | | 726/20 |
| 2015/0245782 A1* | 9/2015 | Morland | A61B 5/0095 |
| | | | 600/301 |
| 2016/0038055 A1* | 2/2016 | Wheeler | A61B 5/681 |
| | | | 600/547 |
| 2016/0071393 A1* | 3/2016 | Kaplan | B60K 28/066 |
| | | | 340/539.12 |
| 2017/0181703 A1* | 6/2017 | Kaib | A61N 1/3943 |
| 2017/0265810 A1* | 9/2017 | Van De Vyver | A61B 5/6833 |
| 2018/0211020 A1* | 7/2018 | Fukuda | G06K 9/00013 |

FOREIGN PATENT DOCUMENTS

| | | | | |
|---|---|---|---|---|
| WO | WO 2016030752 A1 * | 3/2016 | | A61B 5/6833 |
| WO | WO-2016049859 A1 * | 4/2016 | | G06F 1/32 |

OTHER PUBLICATIONS

M. Roller "Beschreibung Eines Systems Zur Messung Der Tragezeit Ortopädischer Hilfsmittel", Orthopädie Technik (Dec. 1, 2013) URL: http://www.orthotimer.com/downloads.d/ot.pdf.

"Neuheiten für Analyse und Fertigung", Orthopädie Schuhtechnik, Neue Technologien, (Jul. 8, 2014) URL: http://www.orthotimer.com/downloads.d/orthopaedie-schuhtechnik_082014.pdf.

"Orthotimer" Weltneuheit: Orthotimer Compliance Messsystem (Jan. 1, 2014) URL: http://www.orthotimer.com/downloads.d/interview-matthias-roller.pdf.

Havey Robert et al., "A Reliable and Accurate Method for Measuring Orthosis Wearing Time" Spine, vol. 27 No. 2 (Jan. 15, 2002) pp. 211-214.

Jan. 19, 2017 Search Report issued in French Patent Application No. 1654389.

* cited by examiner

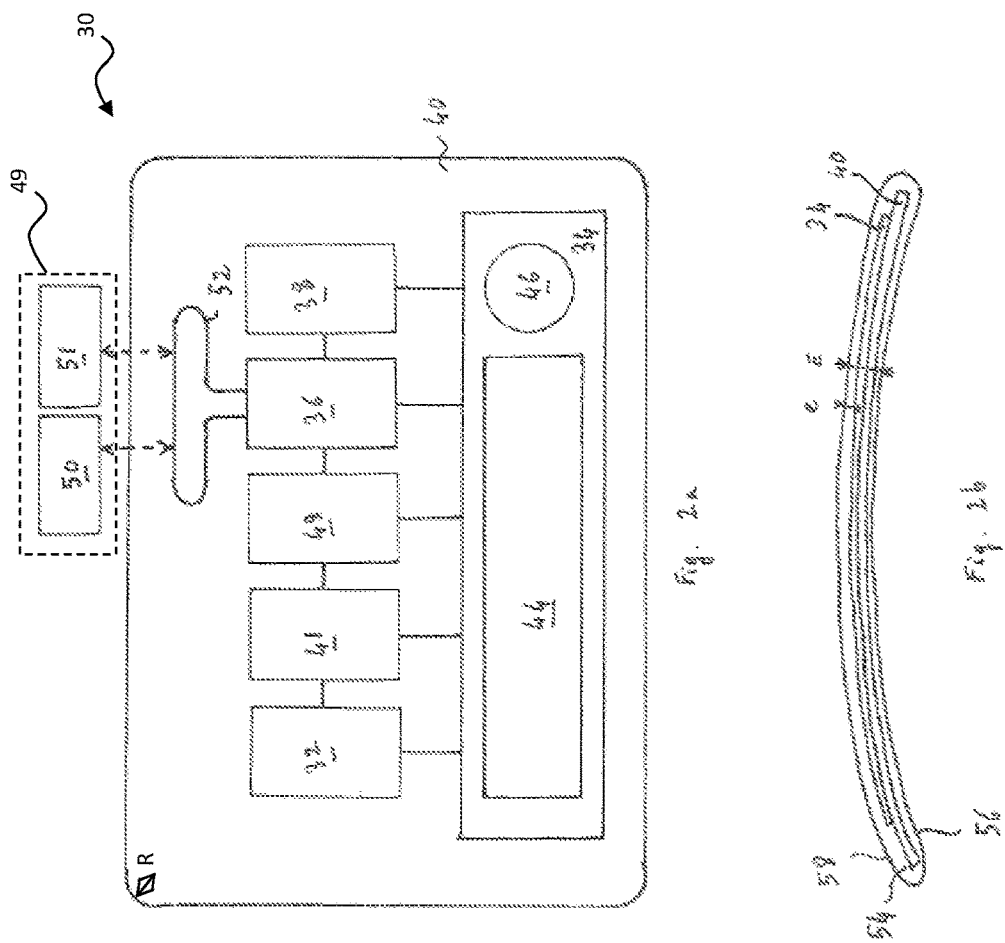
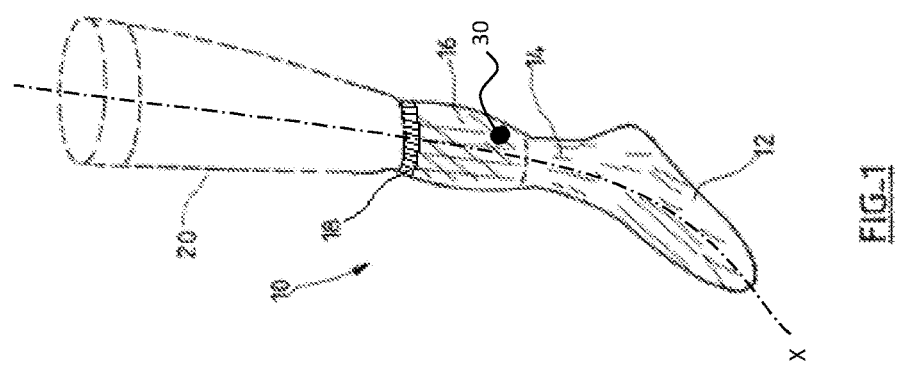

ELASTIC VENOUS COMPRESSION ORTHOSIS

TECHNICAL FIELD

The present invention relates to an elastic venous compression orthosis indicated in cases of venous insufficiency in a lower limb of a patient.

PRIOR ART

Elastic venous compression orthoses, formerly known as "retention stockings (or hoses)" or "retention tights", are textile medical devices for producing a therapeutic effect by way of compressing the lower limbs, unlike "support stockings" (or even "support hoses" or "anti-fatigue stockings") and "fashion stockings," which are not medical devices for therapeutic purposes.

Elastic venous compression orthoses are designed to produce a therapeutic effect by way of compressing the lower limb over an area of variable size, usually with a compression profile that decreases upwards from the ankle.

The effectiveness of a treatment with an orthosis is directly connected to patient compliance with the medical prescription. Without good compliance, the disease can worsen, resulting in additional risks for the patient, as well as costs for Social Security or health care funding agencies.

Poor compliance with the treatment also makes clinical studies more difficult, especially if the patient does not report periods of noncompliance.

Lastly, the improvement of orthoses requires precise identification of the conditions under which the orthoses are worn.

Conventionally, questionnaires have been used to verify compliance. The answers are, however, imprecise or even incorrect.

There is therefore a need for a solution that allows for improved compliance and allows knowledge of the conditions under which an orthosis is worn.

An object of the invention is to respond to this need, at least partially.

SUMMARY OF THE INVENTION

The invention provides an orthosis intended to be worn in contact with the skin of a patient, and in particular an elastic venous compression orthosis that is notably provided with a device for measuring the time during which the orthosis is worn.

The invention also relates to such a measurement device, which may advantageously be attached to an orthosis. In particular, the invention relates to a device for measuring the time during which an elastic venous compression orthosis is worn, the device comprising a capacitive sensor regulated so as to transmit a detection signal only when the value of a capacitance of the capacitive sensor is in an operating range, the operating range comprising, and preferably consisting of, possible values for the capacitance when the orthosis is operating. Such a measurement device may also comprise one or more of the optional features described below for the device provided on an orthosis according to the invention.

The data measured by the device may advantageously be used to gain accurate information on treatment compliance. This information is useful for the patient, who can thereby better use the orthosis, but also for the manufacturer, who can thereby improve the orthosis, and for the prescriber, who can thereby confirm that the treatment is properly followed.

An orthosis according to the invention may further comprise one or more of the following optional features:
- the device comprises a capacitive sensor regulated so as to transmit a detection signal when the value of a capacitance of the capacitive sensor is in an operating range, and preferably exclusively when the value of a capacitance of the capacitive sensor is in an operating range;
- the device comprises means for monitoring the measurement conditions, the monitoring means preferably comprising a temperature sensor, and/or a pressure sensor, and/or a force sensor;
- the measurement device is free of sharp corners;
- the measurement device comprises a communications module, preferably a radio frequency communications module;
- the measurement device comprises an encapsulating material for hermetically sealing the electronic components of the measurement device from the exterior;
- the measurement device has at least one large curved face, which is preferably concave; and
- the orthosis is an elastic venous compression orthosis.

The invention also provides a kit comprising:
- an orthosis according to the invention and an external module, in particular a computer, and/or a mobile telephone, and/or a tablet, the external module comprising a computer program including program code instructions for:
  - establishing communication, preferably remote communication, with the communications module of the measurement device; and/or
  - activating and/or deactivating the measurement device; and/or
  - controlling an exchange of information, and in particular downloading information stored in a memory of the measurement device.

Lastly, the invention relates to a method for improving compliance with a treatment based on use of an elastic venous compression orthosis, and/or for improving the performance of an elastic venous compression orthosis, the method comprising the following successive steps:
a) providing an orthosis according to the invention to a patient;
b) activating the measurement device;
c) downloading data stored in the measurement device, preferably to a computer, or a mobile telephone, or a tablet, preferably after a treatment period of more than a week, and more preferably more than one month, or even more than three months; and
d) analysing the data in order to prepare a compliance assessment, and, preferably, a correlation between compliance, the characteristics of the orthosis, and the therapeutic effect of this orthosis.

BRIEF DESCRIPTION OF THE FIGURES

Other features and advantages of the invention will be apparent from reading the detailed description which follows, and examining the accompanying drawings, in which:

FIG. 1 is a schematic representation of an orthosis according to the invention; and FIG. 2 is a schematic representation of a measurement device according to the invention, in a top view (FIG. 2a) and a front view (FIG. 2b).

DEFINITIONS

"Altitude" corresponds to a level, in the vertical direction, when the orthosis is worn by a patient standing straight upright. The adjectives "upper" and "lower" are also based on this standard.

The "operating position" of an orthosis is a position of use, which is to say a position in which it is worn, particularly pulled onto a lower limb of a patient.

Unless otherwise indicated, "comprising", "including", "having", "involving" and variations thereof correspond to non-exclusive inclusion.

DETAILED DESCRIPTION

In FIG. 1, reference numeral 10 designates overall an orthosis according to the invention.

The orthosis 10, which is generally tubular, includes: a foot portion 12, surrounding the foot; a leg portion 13, comprising an ankle portion 14, surrounding the ankle, and a calf portion 16, surrounding the calf.

If the orthosis is a "knee" (or "calf") sock, the orthosis 10 extends to a level below the knee. In the latter case, the orthosis ends in a terminal knitted part referred to as a "cuff" 18.

There is no limitation to a sock-type configuration, but rather the orthosis 10 may also be configured as a "thigh" stocking, which continues into a compression thigh portion 20. The orthosis 10 may also be configured as tights, and/or may be without a foot portion 12 ("open foot" type stockings or tights).

The various adjoining parts of the orthosis 10 are preferably continuously knitted on a circular knitting machine, according to conventional methods. Fabrication of the orthosis 10 does not require a production step for assembling the various parts, other than sewing operations for the end the foot portion 12, if a foot portion is included.

Measurement Device

According to the invention, the orthosis comprises a device 30 for measuring the time for which the orthosis is worn.

Preferably, the device 30 comprises a sensor, a control module 34, a communications module 36 and a power source, such as a battery 38, which are mounted on a substrate 40, wherein the assembly is preferably encapsulated.

Preferably, the sensor is a capacitive sensor 32 or a combination of capacitive sensors.

In principle, a capacitive sensor measures the effect of a local electric field and detects or measures any change in this local electric field, particularly changes resulting from the capacitive sensor nearing the skin. In particular, a capacitive sensor can transform an electrical disturbance of the electric field into an electric voltage, reflecting the corresponding disturbance.

Capacitive sensors are widely used as industrial sensors.

A capacitive sensor 32 is advantageously easy to incorporate into an orthosis. In particular, unlike an optical sensor, it will work even if it is covered, in particular by an encapsulating material. Furthermore, it works even without being in direct contact with the skin of the patient. Lastly, capacitive sensors are particularly reliable.

The capacitive sensor transmits information, which varies as a function of the capacitive environment of the device, to the control module 34. In particular, in a preferred embodiment, it sends a binary signal that depends on whether or not the capacitance of the sensor capacitor is in a predetermined "operating" range. The operating range is determined in accordance with the effect, on the capacitance, of the lower member on which the capacitive sensor is arranged when operating, and in accordance with other components of the device, and in particular the encapsulating material.

In a preferred embodiment, the device comprises a plurality of sensors 41, and preferably a plurality of sensors 41 of different types (e.g., a temperature sensor, a pressure sensor and/or a force sensor). For example, the device may comprise a temperature sensor. Analysis of data from the various sensors advantageously makes it possible to more precisely determine the conditions under which the measurements were made. For example, when the orthosis is washed, it may become wet, which could lead the capacitive sensor 32 to determine that the orthosis is being worn. If, at the same time, the temperature sensor indicates a temperature that cannot be associated with the body temperature of a patient, this error can be easily corrected.

The pressure sensor and/or the force sensor may also be used for this purpose.

Furthermore, a pressure sensor serves to monitor the state of the orthosis, and, in particular in the compression areas of the orthosis, to confirm that the operating pressure exerted is satisfactory.

The control module 34 typically comprises a microprocessor 44, which can control communications with the outside, via the communications module 36, and can also control the capacitive sensor 32, in order to receive the data measured by the capacitive sensor and store it in a memory 46.

In one embodiment, the control module further comprises a clock 48 for time-stamping the data measured by the capacitive sensor. It is thus advantageously possible not only to measure the wearing time, but also to determine the point in time at which the orthosis was put on.

The measured time may correspond to a counted number of periodically generated pulses. This may be provided as a usage time or a usage rate (ratio between the time of use and the time for which the orthosis was available).

The communications module 36 is known per se and allows activation data, and/or connection data, and/or data measured and recorded by the control module, to be sent to an external module 49, such as a computer 50 and/or a telephone 51, particularly a computer 50 and/or a telephone 51 belonging to a doctor.

The communications module 36 is preferably configured for radio frequency communication complying with communication standards, such as those for RFID, or, preferably, NFC (near-field communication) and, notably, WIFI or BLUETOOTH.

The power source is preferably rechargeable. Preferably, the power source is configured so as to be recharged by thermal energy, preferably by heat generated by the patient, and/or by mechanical energy, preferably energy resulting from body movements of the patient.

In one embodiment, the energy is transmitted via a wireless power transmission technology, such as inductive power transmission.

The power source is preferably flat. It is preferably less than 5 mm thick, more preferably less than 4 mm thick, still more preferably less than 3 mm thick, or even less than 2 mm thick.

In one embodiment, the power source is a battery that is not rechargeable.

The substrate 40 may be of a type that is used for manufacturing printed circuits, such as a polyamide film, for example Kapton®. Electrically conductive leads are printed on the substrate in the conventional manner, particularly between the capacitive sensor, the control module and the communications module.

The substrate is preferably less than 10 cm long, more preferably less than 8 cm long, still more preferably less than 5 cm long, and yet more preferably less than 4 cm long, and/or preferably less than 5 cm wide, more preferably less than 4 cm wide, and still more preferably less than 3 cm wide.

It is also preferable that the substrate be flat, preferably with a contour that is free of sharp corners. In particular, the contour of the substrate may be round, oval or rectangular, the four corners of the rectangular contour being rounded, as shown. Preferably, the radius of curvature R is greater than 0.5 mm, greater than 1 mm, or greater than 2 mm, at all points on the contour of the substrate.

It is also preferable that the substrate has a thickness less than 1 mm, preferably less than 0.5 mm. The substrate may be rigid or flexible. It is preferably flexible, which is to say that it can be bent by hand without particular effort. Preferably, the flexibility is sufficient so that, in the operating position, the substrate takes on the shape of the part of the patient's body with which it is in contact. This improves comfort.

It is also preferable that an antenna 52 is printed on the substrate to allow non-contact communication, preferably radio frequency communication complying with communication standards, such as those for RFID, preferably NFC, and notably WIFI or BLUETOOTH, particularly with the computer 50 and/or the telephone 51.

Preferably, the substrate and the components mounted on the substrate are encapsulated, preferably in a sealed manner, and preferably by a biocompatible material. The biocompatible material can, in particular, be selected from the group consisting of polymers and silicones.

The biocompatibility is preferably in compliance with NF EN ISO 10993-1.

Encapsulation advantageously extends the life of the device, which is subjected to severe stresses when used, and in particular when the orthosis is washed.

The encapsulating material preferably forms a layer with an average thickness, starting from the substrate, of less than 2 mm, preferably less than 1 mm, or even less than 0.5 mm. Preferably, the encapsulating layer defines an outer surface that is smooth to the touch.

Preferably, the encapsulating material is flexible, and preferably bendable by hand. This improves usability. Advantageously, the flexibility also allows a good fit to the shape of the area of the patient's body that is in contact with the device (measurement area).

In a preferred embodiment, the encapsulating material defines two major outer faces 56 and 58, respectively extending over opposite major faces of the substrate. It is also preferable that at least one of the major outer faces, preferably each of the major outer faces, 56 and 58 of the device is curved, preferably so as to have a shape that is substantially complementary to that of the part of the lower member on which it is arranged when in use.

Preferably, the major outer face 56 that is oriented towards the interior of the orthosis, which is to say towards the X axis, is concave.

Preferably, the major outer face 58 that is oriented towards the exterior of the orthosis is convex.

Preferably, the device has a maximum thickness E that is less than 7 mm, more preferably less than 5 mm, and still more preferably less than 3 mm.

The device may be attached to the orthosis by any means. In particular, it may be glued, stapled or sewn. Preferably, the device is mounted so as not to protrude from the outer face of the orthosis when in use. This reduces the risk of the device being pulled off. It also makes the device more discrete.

The device is preferably mounted on the cuff of the orthosis, and in particular, if the cuff comprises two layers of fabric folded over each other, is preferably mounted between the two layers.

Operation

In step a), the orthosis is provided to the patient to be treated.

The measurement device 30, which is integrated into the orthosis 10 and powered by the battery 38, is initially disabled.

In step b), activation, which is to say turning on, is preferably brought about by reception of "activation data" which are sent, preferably in a non-contact manner, and preferably by communication of the NFC type, from the external module 49, which is, for example, a computer or a mobile telephone, having a suitable software application.

Activation may be done by a pharmacist or may occur automatically, for example when the orthosis is removed from its packaging.

In a non-preferred embodiment, the device may also be activated by the patient.

The operating range for the values of the capacitance of the capacitive sensor is configured, preferably before activation, using possible values for the capacitance when the orthosis is in the operating position.

When the orthosis is pulled on by the patient so as to be positioned in the operating position, the environment of the device, and in particular the proximity of the patient's skin, changes the value of the capacitance of the capacitor of the capacitive sensor 32. The value of the capacitance of the sensor thus falls within the operating range. Preferably, the capacitive sensor 32 then periodically sends corresponding basic information. The basic information may be date-stamped by the clock 48. The control module 34 calculates the total count for the basic information.

When the patient removes the orthosis, the value of the capacitance departs from the operating range and the basic information transmitted is no longer taken into account. When the patient once again pulls on the orthosis, the basic information transmitted by the capacitive sensor is once again taken into account, and the control module continues the count. The total count for the basic information is thus proportional to the total time that the orthosis has been worn.

In particular, when the orthosis is washed, the encapsulating material 54 protects the electronic components.

During washing, and especially during drying, the environment can result in errors in which the capacitive sensor 32 determines that the orthosis is in the operating position. Tests have shown that such errors do not substantially alter the results obtained. Notably, the time during which the errors occur is very short, as compared to the wearing time.

However, to improve accuracy, the second sensor 41 (e.g., a temperature sensor, a pressure sensor and/or a force sensor) may provide another measurement, particularly a temperature measurement, or another capacitive sensor for detecting the error, and thus filtering out erroneous data.

In step c), the measured data are downloaded, for example to the external module 49.

The data recorded by the control module 34 may be sent in real time, and/or at regular intervals, to the external module 49. Preferably, however, they are stored in the memory 46 until NFC communication is established. Notably, the connection may be brought about by reception of "connection data" sent from the external module. Preferably, the external module is a telephone or a dedicated terminal. Downloading of the data may notably be performed when the patient returns to see their doctor, with the orthosis, preferably performed by the patient or by the doctor.

In step d), analysis of data received by the control module (data measured by the various sensors, and time stamp data) may be performed by the microprocessor 44 of the control module and/or the external module, after the data have been sent by the communications module 36.

Depending on the amount of data, it is possible to determine not only the "wearing time," but also, in particular, the time periods when the orthosis was worn, and/or the conditions in which the orthosis was worn.

The analysis can also result in evaluation of the total wearing time, and/or the number of washes, and/or the washing conditions, and/or, if the measurement device comprises a pressure sensor, the pressure locally exerted by the orthosis. In one embodiment, analysis of this information makes it possible to indicate whether the orthosis should be replaced, particularly if it is no longer effective.

In one embodiment, all the data concerning a patient for a given period are consolidated, in particular to allow for the use of several orthoses during that period.

The doctor may analyse the data to improve the treatment, and/or send the data to the orthosis manufacturer, preferably anonymously, so that the manufacturer can improve the properties. In one embodiment, the doctor also sends information concerning the effectiveness of the treatment, and/or concerning patient experience, particularly in terms of comfort. The manufacturer can thus establish connections between the characteristics of the orthosis and this information, which makes it possible to improve the orthosis more rapidly.

The analysis may result in a diagnostic report, preferably providing recommendations to the patient, for example indicating that the wearing time is insufficient, or that the orthosis is not worn properly or needs to be replaced.

If the recorded data are time-stamped, the analysis can also detect the periods during which the orthosis is worn, but also the time between activation and the first use of the orthosis.

As will now be clear, the invention provides a solution not only allowing for improved compliance, but also allowing knowledge of the conditions under which an orthosis is worn.

This solution is particularly advantageous in cases where a capacitive sensor is used, as is preferred.

Unlike other known sensors, capacitive sensors are in fact particularly well suited to applications in elastic venous compression orthoses. They make it possible to satisfy all of the specific requirements for this application:
- the ability to differentiate between the presence and absence of a leg in contact with the orthosis;
- the ability to detect washing of the venous compression orthosis;
- the ability to be encapsulated;
- strength, particularly after encapsulation, over a period of several months, and in harsh environments, in which the orthosis must be worn, washed and stored;
- the ability to function without being in direct contact with the patient's leg, particularly so as to avoid biocompatibility problems;
- the ability to be integrated without substantially changing the comfort of the orthosis;
- low power consumption, which allows for sufficient autonomy; and
- the ability to be commercially produced at a low unit cost.

In particular, in the operating position, measurement with a force or pressure sensor, such as a strain gauge integrated into the stocking, or a resistive force sensor, or by a shape or elongation sensor, such as a resistive curvature sensor or coil-shaped inductive sensor, will be influenced by the tension on the orthosis, which is exerted by the elasticity of the threads. This impacts the measurement reliability.

In the operating position, measurement by a temperature sensor, such as a thermistor or an optical sensor for infrared measurement, is influenced by the skin temperature of the leg. This impacts the measurement reliability.

An optical sensor is reactive to a modification or a crossing of a light beam, which makes its integration in an orthosis more difficult. In addition, the use of an optical sensor makes difficult the distinction between the phases during which the orthosis is worn and the phases during which it is being cleaned or stored.

Of course, the invention is not limited to the embodiments described and shown, which are provided for illustrative purposes only.

In particular, multiple external modules may be used to activate the measurement device, connect the measurement device, and download the stored data or analyse data that has been received.

Furthermore, the invention is directed to an elastic venous compression orthosis, but is not limited to such an application. The invention does not, however, relate to implanted medical devices. An orthosis according to the invention is worn on the skin.

The invention claimed is:

1. A method for measuring compliance with a treatment based on use of an elastic venous compression orthosis, intended to be worn in contact with a body of a patient, and/or for improving a performance of the elastic venous compression orthosis, the method comprising the following successive steps:
   providing, to the patient, the elastic venous compression orthosis, the orthosis being provided with a measurement device, the measurement device being rigidly fixed on the orthosis, the measurement device being mounted between two layers of fabric folded over each other, the measurement device comprising:
   a communication module configured to communicate at a radio frequency;
   a capacitive sensor configured to transmit first data when a value of a capacitance of the capacitive sensor is in an operating range, the operating range being calibrated such that the value of the capacitance of the capacitive sensor is within the operating range when the orthosis is being worn, and the value of the capacitance departs from the operating range when the orthosis is not worn;
   a temperature sensor configured to: (a) detect a temperature of the body of the patient to determine whether the orthosis is being worn during a possible washing of the orthosis, and (b) transmit second data related to the detection of the temperature of the body;
   a microprocessor configured to:
   store a clock;
   receive the first data from the capacitive sensor,
   receive the second data from the temperature sensor, time-stamp the first data received from the capacitive sensor for measuring a wearing time and when the orthosis is worn based on the clock, and filter the first data from the capacitive sensor in response to the orthosis not being worn based on the second data from the temperature sensor;

a substrate on which the microprocessor, the communication module, the capacitive sensor, and the temperature sensor are mounted; and an encapsulating material that hermitically seals an entirety of: (i) the microprocessor, (ii) the communication module, (iii) the capacitive sensor, (iv) the temperature sensor, and (v) the substrate, so as to protect the measurement device during the possible washing of the orthosis;

activating the measurement device;

after a treatment period of more than a week, establishing a remote communication between the communication module of the measurement device and an external module and downloading, in the external module, at least the filtered first data and the second data stored in the measurement device for compliance assessment; and analysing, by the external module, the filtered first data and the second data including:

determining the wearing time or time periods when the orthosis is worn based on the time-stamp of the filtered first data and determining the temperature of the body.

2. The method according to claim 1, wherein the measurement device further comprises at least one of a force sensor or another capacitive sensor.

3. The method according to claim 1, wherein the measurement device is free of sharp corners.

4. The method according to claim 1, wherein the communication module is a radio frequency communications module.

5. The method according to claim 1, wherein the measurement device has at least one large curved face.

6. The method according to claim 1, the method further comprising a step of programming the microprocessor to include program code instructions for:

establishing remote communication with the communication module of the measurement device; and/or providing the activating of the measurement device, and/or deactivating the measurement device; and/or controlling an exchange of information, the exchange including the downloading, in the external module, of the filtered first data stored in the measurement device.

7. The method according to claim 1, wherein the external module is a computer, a mobile phone, or a tablet.

8. The method according to claim 1, wherein the treatment period is more than a month.

9. The method according to claim 1, wherein the treatment period is more than three months.

10. The method according to claim 1, wherein the measurement device is glued, stapled or sewn on the orthosis.

11. The method according to claim 1, wherein the substrate of the measurement device includes a pressure sensor configured to detect a pressure locally exerted by the orthosis.

12. A method for measuring compliance with a treatment based on use of an elastic venous compression orthosis, intended to be worn in contact with a body of a patient, and/or for improving a performance of the elastic venous compression orthosis, the method comprising the following successive steps:

providing, to the patient, the elastic venous compression orthosis, the orthosis being provided with a measurement device, the measurement device being rigidly fixed on the orthosis, the measurement device being mounted between two layers of fabric folded over each other, the measurement device comprising:

a communication module configured to communicate at a radio frequency;

a capacitive sensor configured to transmit first data when a value of a capacitance of the capacitive sensor is in an operating range, the operating range being calibrated such that the value of the capacitance of the capacitive sensor is within the operating range when the orthosis is being worn, and the value of the capacitance departs from the operating range when the orthosis is not worn;

a pressure sensor configured to: (a) detect a pressure locally exerted by the orthosis to determine whether the orthosis is being worn during a possible washing of the orthosis, and (b) transmit second data related to the detection of the pressure locally exerted by the orthosis;

a microprocessor configured to:

store a clock;

receive the first data from the capacitive sensor, receive the second data from the pressure sensor, time-stamp the first data received from the capacitive sensor for measuring a wearing time and when the orthosis is worn based on the clock, and filter the first data from the capacitive sensor in response to the orthosis not being worn based on the second data from the pressure sensor;

a substrate on which the microprocessor, the communication module, the capacitive sensor, and the pressure sensor are mounted; and an encapsulating material that hermitically seals an entirety of: (i) the microprocessor, (ii) the communication module, (iii) the capacitive sensor, (iv) the pressure sensor, and (v) the substrate, so as to protect the measurement device during the possible washing of the orthosis;

activating the measurement device;

after a treatment period of more than a week, establishing a remote communication between the communication module of the measurement device and an external module and downloading, in the external module, at least the filtered first data and the second data stored in the measurement device for compliance assessment; and analysing, by the external module, the filtered first data and the second data including:

determining the wearing time or time periods when the orthosis is worn based on the time-stamp of the filtered first data and determining an operating pressure at which the orthosis is worn.

13. The method according to claim 12, wherein the substrate of the measurement device includes a temperature sensor configured to detect a temperature of the body of the patient.

14. A method for measuring compliance with a treatment based on use of an elastic venous compression orthosis, intended to be worn in contact with a body of a patient, and/or for improving a performance of the elastic venous compression orthosis, the method comprising the following successive steps:

providing, to the patient, the elastic venous compression orthosis, the orthosis being provided with a measurement device, the measurement device being rigidly fixed on the orthosis, the measurement device being mounted between two layers of fabric folded over each other, the measurement device comprising:
- a communication module configured to communicate at a radio frequency;
- a capacitive sensor configured to transmit first data when a value of a capacitance of the capacitive sensor is in an operating range, the operating range being calibrated such that the value of the capacitance of the capacitive sensor is within the operating range when the orthosis is being worn, and the value of the capacitance departs from the operating range when the orthosis is not worn;
- a temperature sensor configured to: (a) detect a temperature of the body of the patient to determine whether the orthosis is being worn during a possible washing of the orthosis, and (b) transmit second data related to the detection of the temperature of the body;
- a microprocessor configured to:
  store a clock;
  receive the first data from the capacitive sensor,
  receive the second data from the temperature sensor,
  time-stamp the first data received from the capacitive sensor for measuring a wearing time and when the orthosis is worn based on the clock, and
  filter the first data from the capacitive sensor in response to the orthosis not being worn based on the second data from the temperature sensor;
- a substrate on which the microprocessor, the communication module, the capacitive sensor, and the temperature sensor are mounted; and
- an encapsulating material that hermitically seals an entirety of: (i) the microprocessor, (ii) the communication module, (iii) the capacitive sensor, (iv) the temperature sensor, and (v) the substrate, so as to protect the measurement device during the possible washing of the orthosis;

activating the measurement device;
after a treatment period of more than a week, establishing a remote communication between the communication module of the measurement device and an external module and downloading, in the external module, at least the filtered first data and the second data stored in the measurement device for compliance assessment; and
analysing, by the external module, the filtered first data and the second data including:
  determining the wearing time or time periods when the orthosis is worn based on the time-stamp of the filtered first data and determining the temperature at which the orthosis is worn.

* * * * *